United States Patent
Fleckenstein et al.

(10) Patent No.: US 6,291,681 B1
(45) Date of Patent: Sep. 18, 2001

(54) PROCESS FOR PREPARING BIOTIN

(75) Inventors: Juergen Fleckenstein, Wehr; Bernd Kraemer, Schopfheim, both of (DE); Joachim Veits, Florence, SC (US)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/780,253

(22) Filed: Feb. 9, 2001

(30) Foreign Application Priority Data

Feb. 25, 2000 (CH) .................................................. 0374/00

(51) Int. Cl.$^7$ ................................................. C07D 233/32
(52) U.S. Cl. .......................................................... 548/322.5
(58) Field of Search ........................................... 548/322.5

(56) References Cited

U.S. PATENT DOCUMENTS 5,151,525 * 9/1992 Seiter et al. ......................... 548/321

FOREIGN PATENT DOCUMENTS 51-8270   1/1976  (JP) .

* cited by examiner

*Primary Examiner*—Floyd D. Higel
*Assistant Examiner*—Golam M. M. Shameem
(74) *Attorney, Agent, or Firm*—Stephen M. Haracz; Bryan Cave

(57) ABSTRACT

The present invention is directed to a process for the production of 2-oxo-1,3-dibenzyl-cis-4,5-imidazolidinedicarboxylic acid and of 2-oxo-1,3-dibenzyl-cis-4,5-imidazolidinedicarboxylic acid anhydride, starting from meso-2,3-bis(benzylamino)succinic acid dialkali metal salt. The process involves reacting meso-2,3-bis(benzylamino)succinic acid dialkali metal salt with phenyl chloroformate in a monophasic solvent system consisting of an about 2:1 to 1:1 mixture of a water-miscible ether and an aqueous alkali metal hydroxide solution, at a temperature not exceeding about 40° C. The resulting 2-oxo-1,3-dibenzyl-cis-4,5-imidazolidinedicarboxylic acid dialkali metal salt is converted, by acidification, into the desired 2-oxo-1,3-dibenzyl-cis-4,5-imidazolidinedicarboxylic acid, which is then either isolated, or converted, by heating with acetic anhydride, in an aromatic hydrocarbon as the organic solvent, into the desired 2-oxo-1,3-dibenzyl-cis-4,5-imidazolidinedicarboxylic acid anhydride, which is in turn, isolated. Each product is an important intermediate in the multi-stage process for the manufacture of biotin (vitamin H).

25 Claims, No Drawings

PROCESS FOR PREPARING BIOTIN

FIELD OF THE INVENTION

The present invention relates to a process for the production of 2-oxo-1,3-dibenzyl-cis-4,5-imidazolidinedicarboxylic acid, and of the corresponding anhydride.

BACKGROUND OF THE INVENTION

The production of 2-oxo-1,3-dibenzyl-cis-4,5-imidazolidinedicarboxylic acid, starting from meso-2,3-bis(benzylamino)succinic acid in the form of its dialkali metal salt, is known in the art. For example, Seiter, U.S. Pat. No. 5,151,525 ("Seiter '525") discloses a process in which phosgene is used as the reagent, in an alkaline-aqueous/organic two-phase solvent system, that causes the linkage of the two secondary nitrogen atoms via a carbonyl group resulting in ring formation. The reaction disclosed in Seiter '525 employs anisole as the essentially water-immiscible solvent.

The phosgene reagent of Seiter '525, however, is highly toxic and potentially explosive under the influence of other gases or certain reaction liquids. Thus, its use is extremely dangerous when carelessly handled, or supervised, and special precautions are required in its transport, storage and use, e.g., the use of safety devices is essential in any apparatus that comes into contact with phosgene.

A process for the production of the aforementioned cyclo acid that also starts from meso-2,3-bis(benzylamino) succinic acid in the form of its dialkali metal salt, but using an alkyl, haloalkyl or aryl chloroformate in place of phosgene for the ring formation, is disclosed in Japanese Patent Publication (Kokai) No. 8270/1976 ("JP 8270/1976"). Although the disclosed process avoids the disadvantages of phosgene outlined above, it still has other equally serious disadvantages, which may explain why the use of chloroformates has hitherto not been adopted. Apart from the high costs involved, some other disadvantages of using chloroformate are, for example, the production of diphenyl carbonate and phenol as unavoidable byproducts. The diphenyl carbonate separates as a viscous mass from the aqueous reaction solution and clogs up the reactor components and the pH probe. For this reason, pH values cannot be reported accurately, which is of critical significance for the controlled performance of the reaction. However, the cyclo acid can only be produced in the desired yield by using phenyl chloroformate, which is the preferred reagent according to the examples disclosed in JP 8270/1976.

The first reaction step of the process disclosed in JP 8270/1976 involves the reaction of phenyl chloroformate with meso-2,3-bis(benzylamino)succinic acid dialkali metal salt, along with the cleavage by hydrochloric acid, forming a monourethane intermediate, which then reacts further to form the cyclo acid. The resulting alkali phenolate reacts with phenyl chloroformate to form the byproduct diphenyl carbonate. The remaining hydrochloric acid can be neutralized by the addition of alkali metal hydroxide solution, whereby the pH value should be neither too low nor too high. If the pH is too low, the meso-2,3-bis(benzylamino) succinic acid precipitates out and cannot be reacted. Moreover, the meso-2,3-bis(benzylamino)succinic acid combines with separated diphenyl carbonate to form a viscous mass, leading to further clogging of the reactor components, including the stirrer. If the pH is too high, the phenyl chloroformate hydrolyzes too rapidly, leading to unnecessary consumption.

Furthermore, the precipitation of the cyclo acid by the addition of a strong acid is difficult to accomplish, since this often separates as a viscous mass, as disclosed in JP 8270/1976, and can result in a further clogging of the reactor components, including the stirrer.

SUMMARY OF THE INVENTION

Accordingly, one object of the present invention is a process for the production of 2-oxo-1,3-dibenzyl-cis-4,5-imidazolidinedicarboxylic acid starting from meso-2,3-bis(benzylamino)succinic acid, in the form of its dialkali metal salt, which avoids both the use of phosgene as the reagent for the ring formation, and the considerable disadvantages of performing the process according to the aforementioned Japanese Patent Publication.

This object is achieved by carrying out the reaction of meso-2,3-bis(benzylamino)succinic acid dialkali metal salt with phenyl chloroformate in a mixture of a water-miscible ether and water under alkaline conditions, by which means it is possible to keep the diphenyl carbonate, which is formed in the reaction, in solution. Accordingly, the reaction is performed in a monophasic solvent system which is free from solid byproducts, thus avoiding clogging of the reactor components, including the stirrer.

Another object of the present invention is a process for the production of 2-oxo-1,3-dibenzyl-cis-4,5-imidazolidinedicarboxylic acid anhydride in which, after carrying out the process as set forth above for the production of 2-oxo-1,3-dibenzyl-cis-4,5-imidazolidinedicarboxylic acid starting from a meso-2,3-bis(benzylamino)succinic acid dialkali metal salt, but before the resulting 2-oxo-1,3-dibenzyl-cis-4,5-imidazolidinedicarboxylic acid is isolated, this 2-oxo-1,3-dibenzyl-cis-4,5-imidazolidinedicarboxylic acid is converted, by heating with acetic anhydride in an aromatic hydrocarbon as the organic solvent, preferably toluene, into the desired 2-oxo-1,3-dibenzyl-cis-4,5-imidazolidinedicarboxylic acid anhydride, which is then isolated.

Accordingly, one embodiment of the invention is a process for the production of 2-oxo-1,3-dibenzyl-cis-4,5-imidazolidinedicarboxylic acid starting from a meso-2,3-bis(benzylamino)succinic acid dialkali metal salt. This process includes (a) reacting meso-2,3-bis(benzylamino)succinic acid dialkali metal salt with phenyl chloroformate in a monophasic solvent system consisting of an about 2:1 to 1:1 mixture of a water-miscible ether and an aqueous alkali metal hydroxide solution at a temperature not exceeding about 40° C., (b) converting the resulting 2-oxo-1,3-dibenzyl-cis-4,5-imidazolidinedicarboxylic acid dialkali metal salt by acidification into 2-oxo-1,3-dibenzyl-cis-4,5-imidazolidinedicarboxylic acid, and (c) isolating the 2-oxo-1,3-dibenzyl-cis-4,5-imidazolidinedicarboxylic acid.

Another embodiment of the invention is a process for the production of 2-oxo-1,3-dibenzyl-cis-4,5-imidazolidinedicarboxylic acid or 2-oxo-1,3-dibenzyl-cis-4,5-imidazolidinedicarboxylic acid anhydride starting from a meso-2,3-bis(benzylamino)succinic acid dialkali metal salt. This process includes (a) reacting meso-2,3-bis(benzylamino)succinic acid dialkali metal salt with phenyl chloroformate in a monophasic solvent system consisting of an about 2:1 to 1:1 mixture of a water-miscible ether and aqueous alkali metal hydroxide solution at a temperature not exceeding about 40° C., (b) converting the resulting 2-oxo-1,3-dibenzyl-cis-4,5-imidazolidinedicarboxylic acid dialkali metal salt by acidification into 2-oxo-1,3-dibenzyl-cis-4,5-imidazolidinedicarboxylic acid, and (c) isolating the 2-oxo- 1,3-dibenzyl-cis-4,5-imidazolidinedicarboxylic acid or converting the 2-oxo-1,3-dibenzyl-cis-4,5-imidazolidinedicarboxylic acid in step b) to into 2-oxo-1,3-dibenzyl-cis-4,5-imidazolidinedicarboxylic acid anhydride by heating with acetic anhydride in an aromatic hydrocarbon as the organic solvent; and isolating the 2-oxo-1,3-dibenzyl-cis-4,5-imidazolidinedicarboxylic acid anhydride.

And, a further embodiment of the invention is a process for the production of biotin. This process includes (a) providing an intermediate in the biotin production pathway by (i) reacting a meso-2,3-bis(benzylamino)succinic acid dialkali metal salt with phenyl chloroformate in a monophasic solvent system consisting of an about 2:1 to 1:1 mixture of a water-miscible ether and aqueous alkali metal hydroxide solution at a temperature not exceeding about 40° C., (ii) converting the resulting 2-oxo-1,3-dibenzyl-cis-4,5-imidazolidinedicarboxylic acid dialkali metal salt by acidification into 2-oxo-1,3-dibenzyl-cis-4,5-imidazolidinedicarboxylic acid, and (iii) isolating the 2-oxo-1,3-dibenzyl-cis-4,5-imidazolidinedicarboxylic acid or converting the 2-oxo-1,3-dibenzyl-cis-4,5-imidazolidinedicarboxylic acid in step (ii) to into 2-oxo-1,3-dibenzyl-cis-4,5-imidazolidinedicarboxylic acid anhydride by heating with acetic anhydride in an aromatic hydrocarbon as the organic solvent; and isolating the 2-oxo-1,3-dibenzyl-cis-4,5-imidazolidinedicarboxylic acid anhydride. In another step in the process, the 2-oxo-1,3-dibenzyl-cis-4,5-imidazolidinedicarboxylic acid or the 2-oxo-1,3-dibenzyl-cis-4,5-imidazolidinedicarboxylic acid anhydride is used for further reactions in the biotin production pathway.

DETAILED DESCRIPTION OF THE INVENTION

The present invention is directed to a process for producing 2-oxo-1,3-dibenzyl-cis-4,5-imidazolidinedicarboxylic acid starting from a meso-2,3-bis(benzylamino)succinic acid dialkali metal salt. The 2-oxo-1,3-dibenzyl-cis-4,5-imidazolidinedicarboxylic acid and its corresponding anhydride are important intermediates in the multi-stage process for the manufacture of biotin (vitamin H) as described in, for example, the review article of Pierre J. de Clercq in Chem. Rev. 97, 1755–1792 (1997).

The process of the present invention includes reacting the meso-2,3-bis(benzylamino)succinic acid dialkali metal salt with phenyl chloroformate in a monophasic solvent system consisting of an about 2:1 to 1:1 mixture (parts by volume) of a water-miscible ether and aqueous alkali metal hydroxide solution at a temperature not exceeding about 40° C., converting the resulting 2-oxo-1,3-dibenzyl-cis-4,5-imidazolidinedicarboxylic acid dialkali metal salt, by acidification, into the desired 2-oxo-1,3-dibenzyl-cis-4,5-imidazolidinedicarboxylic acid, and isolating this end product.

Examples of water-miscible ethers are tetrahydrofuran and ethylene glycol ethers, e.g., glyme and diglyme, preferably tetrahydrofuran.

The following reaction scheme is a structural representation of the process in accordance with the invention:

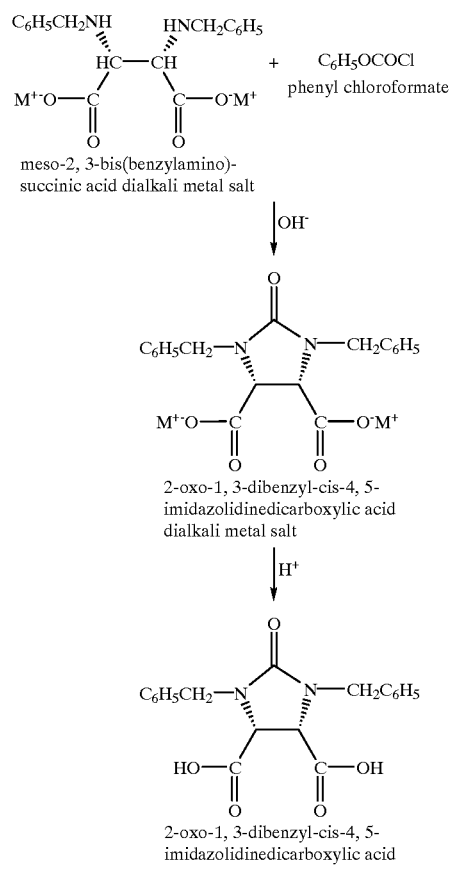

In the above reaction scheme, the alkali metal ion, $M^+$, is preferably a lithium, sodium or potassium ion, more preferably a potassium ion, such that the dilithium, disodium or dipotassium salt, preferably the dipotassium salt, is conveniently used as the starting material for the process in accordance with the invention.

For the production of the meso-2,3-bis(benzylamino)succinic acid dialkali metal salt, the acid is conveniently suspended in water, preferably deionized water, and the resulting suspension is treated with an alkali metal hydroxide solution, preferably a lithium, sodium or potassium hydroxide solution, more preferably a potassium hydroxide solution, preferably at a pH value of about 9 to about 14, more preferably at a pH value of about 12 to about 13. This gives an alkaline-aqueous solution of the desired dialkali metal salt. The concentration of the alkali metal hydroxide solution is not critical, although it amounts to about 40–50 weight percent when a commercial alkali metal hydroxide solution, e.g., a potassium hydroxide solution, is used. Suitable amounts of water and alkali metal hydroxide solution are used in order to ensure that the concentration of the meso-2,3-bis(benzylamino)succinic acid dialkali metal salt is in the range of about 5 to about 20 weight percent, preferably about 10 to about 15 weight percent, based on the total weight of the resulting clear alkaline-aqueous solution, which is at a pH of about 9 to about 14. In order to produce the required alkaline-aqueous ether solution, the water-miscible ether can, if desired, already be present in the suspension of the meso-2,3-bis(benzylamino)succinic acid, such that the acid is effectively suspended in aqueous ether.

Alternatively, the ether can be added for the first time after preparation of the aqueous dialkali metal salt solution.

The combination of the alkaline-aqueous ether solution of the meso-2,3-bis(benzylamino)succinic acid dialkali metal salt with the phenyl chloroformate can be effected in any desired sequence, preferably the phenyl chloroformate is added to the dialkali metal salt solution. It has been found to be advantageous to add the phenyl chloroformate slowly and continuously, i.e., in a stream. During the addition, the pH value of the reaction mixture is held as constant as possible by the addition of an alkali metal hydroxide solution. In order to achieve good intermixing during the addition, the mixture is stirred or otherwise intermixed. Preferably, the combination is effected at about room temperature. However, if desired, both the solution and the phenyl chloroformate can be previously warmed to a slightly elevated temperature of about 30–40° C.

The meso-2,3-bis(benzylamino)succinic acid dialkali metal salt:phenyl chloroformate molar ratio is preferably about 1:1 to about 1:4, more preferably about 1:2 to about 1:3.

During the reaction of the phenyl chloroformate with the meso-2,3-bis(benzylamino)succinic acid dialkali metal salt, the pH value of the reaction mixture is maintained in the range of about 8 to about 14, preferably in the range of about 9 to about 11. To maintain this pH range, aqueous lithium, sodium or potassium hydroxide solution is added at the same time as the reactants are combined. The concentration of the lithium, sodium or potassium hydroxide solution to be added is not critical, preferably the concentration is from about 20 to about 50 weight percent. For this purpose, it is preferable to use the same lithium, sodium or potassium hydroxide solution that was used for the production of the meso-2,3-bis(benzylamino)succinic acid dialkali metal salt.

The reaction is effected at a temperature not exceeding about 40° C., preferably at a temperature in the range of about 25° C. to about 35° C., more preferably at about 30° C. The pressure is not critical, although the reaction is preferably carried out under atmospheric pressure or a slightly elevated pressure.

The process in accordance with the invention is preferably effected under an inert gas atmosphere. When an inert gas atmosphere is used, the inert gas is preferably nitrogen or argon, more preferably nitrogen, when the process is conducted on an industrial scale.

Normally, the reaction has been completed by the time the aforementioned addition has been effected, which usually takes about 2 to 5 hours. The resulting monophasic mixture, which contains the 2-oxo-1,3-dibenzyl-cis-4,5-imidazolidinedicarboxylic acid dialkali metal salt as the product, is rendered slightly alkaline by the addition of acid, preferably to a pH of about 7 to about 8, and extracted with an aromatic hydrocarbon, preferably toluene or xylene. A mineral acid, e.g., hydrochloric acid, hydrobromic acid or sulphuric acid, preferably hydrochloric acid, is suitable as the acid used for the acidification. The desired product, i.e., the dialkali metal salt, is present in the aqueous phase. Tetrahydrofuran is then added to the separated aqueous phase and the dialkali metal salt is converted by acidification into the free acid and the free acid is taken up in the organic phase. The acid used for the acidification is preferably a mineral acid, more preferably hydrochloric acid, hydrobromic acid or sulphuric acid, most preferably hydrochloric acid. The concentration and amount of acid used are chosen such that the aqueous phase has a final pH value of less than 3, preferably about 1. The organic phase that has been separated from the aqueous phase, and which contains the desired product as the free acid, can, after the addition of an aromatic hydrocarbon, e.g., toluene or xylene, as a solvent, be subjected to distillation under reduced pressure in order to remove the tetrahydrofuran, a small amount of the aromatic solvent, and residual water. The 2-oxo-1,3-dibenzyl-cis-4,5-imidazolidinedicarboxylic acid then precipitates as crystals from the resulting super-saturated solution of the desired product in the anhydrous aromatic solvent. Optionally, crystallization can be triggered by seeding and/or by cooling.

The isolated 2-oxo-1,3-dibenzyl-cis4,5-imidazolidinedicarboxylic acid can then be washed, preferably with water, dried, and, if desired, purified further.

Performing the reaction in a monophasic system and crystallizing from an aromatic hydrocarbon offer the following advantages compared to conventional processes:

Safer performance of the reaction without the precipitation of diphenyl carbonate or meso-2,3-bis (benzylamino)succinic acid;

No clogging of the reactor components, including the stirrer;

Adequate control of pH during the duration of the reaction;

Reduction of the amount of phenyl chloroformate used relative to the standard process;

Reproducible precipitation of the 2-oxo-1,3-dibenzyl-cis-4,5-imidazolidinedicarboxylic acid as a fine particulate solid;

Improved yield.

The present invention further provides that by a simple modification at the end of the process described above, it is possible, for the first time, to convert 2-oxo-1,3-dibenzyl-cis-4,5-imidazolidinedicarboxylic acid to 2-oxo-1,3-dibenzyl-cis-4,5-imidazolidinedicarboxylic acid anhydride, the product of the next step in the synthesis of biotin, without having to isolate the 2-oxo-1,3-dibenzyl-cis-4,5-imidazolidinedicarboxylic acid.

Towards the end of the process described above, i.e., immediately after the distillation of the organic solvents, the 2-oxo-1,3-dibenzyl-cis-4,5-imidazolidinedicarboxylic acid crystallizes out and is isolated. However, the modified process avoids isolating the acid, and instead, involves the addition of another aromatic solvent, preferably toluene, and acetic anhydride. For this purpose, at least one mole, preferably about 1.05 moles to about 1.3 moles, of acetic anhydride per mole of starting material, i.e., meso-2,3-bis (benzylamino)succinic acid dialkali metal salt, are used. Upon subsequent heating to 70° C. to 130° C., preferably about 75° C. to about 95° C., more preferably about 80° C., the 2-oxo-1,3-dibenzyl-cis-4,5-imidazolidinedicarboxylic acid reacts in accordance with the scheme set forth below to give 2-oxo-1,3-dibenzyl-cis-4,5-imidazolidinedicarboxylic acid anhydride, which precipitates from the solution and can be isolated according to methods known per se, e.g., by filtration.

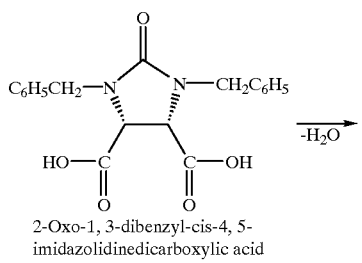

2-Oxo-1, 3-dibenzyl-cis-4, 5-imidazolidinedicarboxylic acid

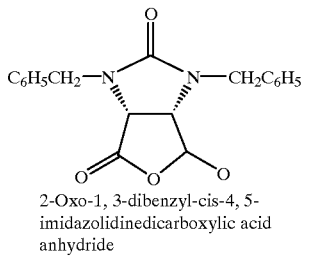

2-Oxo-1, 3-dibenzyl-cis-4, 5-imidazolidinedicarboxylic acid anhydride

The isolated 2-oxo-1,3-dibenzyl-cis-4,5-imidazolidinedicarboxylic acid anhydride can then be washed, preferably with toluene, dried, and if desired, purified further.

Thus, the production of 2-oxo-1,3-dibenzyl-cis-4,5-imidazolidinedicarboxylic acid anhydride in, for example, toluene as the solvent, is exactly the same as the dehydration of 2-oxo-1,3-dibenzyl-cis-4,5-imidazolidinedicarboxylic acid to the anhydride in a mixture of acetic acid and acetic anhydride, a method which has hitherto been used.

The advantages of the process set forth above, that avoids having to isolate 2-oxo-1,3-dibenzyl-cis-4,5-imidazolidinedicarboxylic acid, are:

No isolation of 2-oxo-1,3-dibenzyl-cis-4,5-imidazolidinedicarboxylic acid is required;

The complete and simple crystallization of 2-oxo-1,3-dibenzyl-cis-4,5-imidazolidinedicarboxylic acid anhydride;

A cleaner product;

Reduced expense with respect to apparatus and personnel;

Replacement of acetic acid by toluene;

2-Oxo-1,3-dibenzylamino-cis4,5-imidazolidinedicarboxylic acid need not be dried, discharged and again charged;

No need to adjust and distill mixtures of acetic acid/acetic anhydride;

Reduction of the amount of acetic anhydride used by at least 30%;

Improved yield compared with the yield resulting after completion of the two steps individually.

The following examples are provided to further illustrate the process of the present invention. These examples are illustrative only and are not intended to limit the scope of the invention in any way.

EXAMPLES

Example 1

220 g (0.67 mol) of meso-2,3-bis(benzylamino)succinic acid were placed under a nitrogen atmosphere in a 2 l flask fitted with two dropping funnels, a pH electrode, and a stirrer. The meso-2,3-bis(benzylamino)succinic acid was then suspended, while stirring, in 800 ml of tetrahydrofuran and 400 ml of deionized water and brought into solution by the addition of 108 ml of a 50% potassium hydroxide solution. 200 ml of 2.4 mole q. phenyl chloroformate were added dropwise to the solution within 3.5 hours. The pH was maintained between 9 and 11 during the addition of phenyl chloroformate by the successive addition of a 50% potassium hydroxide solution, and the internal temperature was maintained between 30° C. and 35° C. After the addition was completed, the mixture was stirred at about 30° C. for 2 hours and the pH was adjusted to about 7–8 with concentrated hydrochloric acid. The aqueous solution was then extracted twice with toluene and 500 ml of tetrahydrofuran were added to the combined aqueous phases. The mixture was adjusted to a pH of 1.0 with 37% hydrochloric acid and the aqueous phase was separated off. 400 ml of toluene were added to the tetrahydrofuran phase and the tetrahydrofuran was distilled off under reduced pressure. The remaining water was removed azeotropically with toluene. The residual brownish, oily solution was seeded and the crystalline solid was filtered off and washed twice with toluene. After drying to constant weight under reduced pressure, there were obtained 181.5 g (76% yield) of 2-oxo-1,3-dibenzyl-cis-4,5-imidazolidinedicarboxylic acid, with a melting point of 172.8° C.

Example 2

220 g (0.67 mol) of meso-2,3-bis(benzylamino)succinic acid were placed under a nitrogen atmosphere in a 2 l flask fitted with two dropping funnels, a pH electrode, and a stirrer. The meso-2,3-bis(benzylamino)succinic acid was then suspended, while stirring, in 800 ml of tetrahydrofuran and 400 ml of deionized water, and brought into solution by the addition of 108 ml of a 50% potassium hydroxide solution. 200 ml of 2.4 mole eq. phenyl chloroformate were added dropwise to the solution within 3.5 hours. The pH was maintained between 9 and 11 during the addition of phenyl chloroformate by the successive addition of 50% potassium hydroxide solution and the internal temperature was maintained between 30° C. and 35° C. After the addition was completed, the mixture was stirred at about 30° C. for 2 hours and then the pH was adjusted to about 7–8 with concentrated hydrochloric acid. The aqueous solution was extracted twice with toluene and 500 ml of tetrahydrofuran were added to the combined aqueous phases. The mixture was adjusted to a pH of 1.0 with 37% hydrochloric acid, and the aqueous phase was separated off. 400 ml of toluene were added to the tetrahydrofuran phase and the tetrahydrofuran was distilled off under reduced pressure. The remaining water was removed azeotropically with toluene. After the addition of 700 ml of toluene and 130 ml of acetic anhydride, the mixture was heated to 80° C. After the 2-oxo-1,3-dibenzyl-cis-4,5-imidazolidinedicarboxylic acid anhydride had crystallized out, the obtained suspension was cooled to 10° C. within 2 hours in order to complete the crystallization. The crystalline 2-oxo-1,3-dibenzyl-cis4,5-imidazolidinedicarboxylic acid anhydride was filtered off and washed twice with toluene. After drying to constant weight under reduced pressure, there were obtained 173.6 g (78% yield) of 2-oxo-1,3-dibenzyl-cis4,5-imidazolidinedicarboxylic acid anhydride in the form of an analytically pure, colourless solid, with a melting point of 240.2° C. 3.0 g of 2-oxo-1,3-dibenzylamino-cis4,5-imidazolidinedicarboxylic acid anhydride were further obtained on evaporation of the main solution.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for the production of 2-oxo-1,3-dibenzyl-cis-4,5-imidazolidinedicarboxylic acid or 2-oxo-1,3-dibenzyl-cis-4,5-imidazolidinedicarboxylic acid anhydride starting from a meso-2,3-bis(benzylamino)succinic acid dialkali metal salt, comprising:

a) reacting meso-2,3-bis(benzylamino)succinic acid dialkali metal salt with phenyl chloroformate in a monophasic solvent system consisting of an about 2:1 to 1:1 mixture of a water-miscible ether and aqueous alkali metal hydroxide solution at a temperature not exceeding about 40° C., b) converting the resulting 2-oxo-1,3-dibenzyl-cis-4,5-imidazolidinedicarboxylic acid dialkali metal salt by acidification into 2-oxo-1,3-dibenzyl-cis-4,5-imidazolidinedicarboxylic acid, and c) isolating the 2-oxo-1,3-dibenzyl-cis-4,5-imidazolidinedicarboxylic acid or converting the 2-oxo-1,3-dibenzyl- cis-4,5-imidazolidinedicarboxylic acid in step b) into 2-oxo-1,3-dibenzyl-cis-4,5-imidazolidinedicarboxylic acid anhydride by heating with acetic anhydride in an aromatic hydrocarbon as the organic solvent; and isolating the 2-oxo-1,3-dibenzyl-cis-4,5-imidazolidinedicarboxylic acid anhydride.

2. A process according to claim 1 wherein the aromatic hydrocarbon is toluene.

3. A process according to claim 1 wherein the water-miscible ether is tetrahydrofuran or an ethylene glycol ether.

4. A process according to claim 3 wherein the ethylene glycol ether is glyme or diglyme.

5. A process according to claim 3 wherein the water-miscible ether is tetrahydrofuran.

6. A process according to claim 1 wherein the dialkali metal salt of the meso-2,3-bis(benzylamino)succinic acid dialkali metal salt is selected from the group consisting of dilithium salt, disodium salt, and dipotassium salt.

7. A process according to claim 6 wherein the dialkali metal salt is the dipotassium salt.

8. A process according to claim 1 wherein the meso-2,3-bis(benzylamino)succinic acid dialkali metal salt is prepared by suspending meso-2,3-bis(benzylamino)succinic acid in water and treating the resulting suspension with an alkali metal hydroxide solution to obtain an alkaline-aqueous solution of a dialkali metal salt of the meso-2,3-bis(benzylamino)succinic acid.

9. The process according to claim 8 wherein the alkali metal hydroxide solution is potassium hydroxide solution.

10. A process according to claim 1 wherein the water-miscible ether is added in the preparation of the meso-2,3-bis(benzylamino)succinic acid dialkali metal salt, required as the starting material in step a), before, or after, the production of said dialkali metal salt from meso-2,3-bis(benzylamino)succinic acid and an alkali metal hydroxide solution.

11. A process according to claim 1 further comprising heating the alkaline-aqueous ether solution containing the meso-2,3-bis(benzylamino)succinic acid dialkali metal salt and/or heating the phenyl chloroformate to about 30–40° C. before reaction.

12. A process according to claim 1 wherein the meso-2,3-bis(benzylamino)succinic acid dialkali metal salt:phenyl chloroformate molar ratio is about 1:1 to about 1:4.

13. A process according to claim 12 wherein the meso-2,3-bis(benzylamino)succinic acid dialkali metal salt:phenyl chloroformate molar ratio is about 1:2 to about 1:3.

14. A process according to claim 1 wherein the pH of the reaction mixture is maintained at about 8 to about 14 during the reaction of the meso-2,3-bis(benzylamino)succinic acid dialkali metal salt with the phenyl chloroformate.

15. A process according to claim 14 wherein the pH of the reaction mixture is maintained at about 9 to about 11.

16. A process according to claim 1 wherein the reaction is carried out at about 25° C. to about 35° C.

17. A process according to claim 16 wherein the reaction is carried out at about 30° C.

18. A process according to claim 1 wherein the acidification in step b) is achieved with a mineral acid selected from the group consisting of hydrochloric acid, hydrobromic acid, and sulphuric acid.

19. A process according to claim 18 wherein the mineral acid is hydrochloric acid.

20. A process according to claim 1 further comprising treating the 2-oxo-1,3-dibenzyl-cis-4,5-imidazolidinedicarboxylic acid, without isolation, with an aromatic hydrocarbon and acetic anhydride; and heating the reaction to about 70° C. to about 130° C.

21. A process according to claim 20 wherein the aromatic hydrocarbon is toluene.

22. A process according to claim 20 wherein the reaction mixture is heated to about 75° C. to about 95° C.

23. A process according to claim 22 wherein the reaction mixture is heated to about 80° C.

24. A process according to claim 1 wherein the 2-oxo-1,3-dibenzyl-cis-4,5-imidazolidinedicarboxylic acid is isolated by crystallization from a solution in an aromatic hydrocarbon.

25. A process according to claim 1 wherein the 2-oxo-1,3-dibenzyl-cis-4,5-imidazolidinedicarboxylic acid anhydride is isolated by crystallization from a solution in an aromatic hydrocarbon.

* * * * *

UNITED STATES PATENT AND TRADEMARK OFFICE
CERTIFICATE OF CORRECTION

PATENT NO. : 6,291,681 B1
DATED : September 18, 2001
INVENTOR(S) : Juergen Fleckenstein et al.

It is certified that error appears in the above-identified patent and that said Letters Patent is hereby corrected as shown below:

Column 10,
Line 36, please change the first occurrence of "to" to -- from --.

Signed and Sealed this

Ninth Day of April, 2002

Attest:

Attesting Officer

JAMES E. ROGAN
Director of the United States Patent and Trademark Office